United States Patent [19]

Akiyama et al.

[11] Patent Number: 5,189,148
[45] Date of Patent: Feb. 23, 1993

[54] STABILIZED FGF COMPOSITION AND PRODUCTION THEREOF

[75] Inventors: Yohko Akiyama, Ibaraki; Minoru Yoshioka; Nobuyuki Kitamori, both of Suita, all of Japan

[73] Assignee: Takeda Chemical Industries, Inc., Osaka, Japan

[21] Appl. No.: 547,454

[22] Filed: Jul. 3, 1990

[30] Foreign Application Priority Data

Jul. 7, 1989 [JP] Japan .................................. 1-176228
May 24, 1990 [JP] Japan .................................. 2-136333

[51] Int. Cl.$^5$ .............................................. A61K 37/36
[52] U.S. Cl. ................................... 530/399; 424/477; 424/482; 525/54.1; 530/397
[58] Field of Search ................. 530/397, 399; 514/2, 514/12, 21; 525/54.1; 424/477, 482

[56] References Cited

U.S. PATENT DOCUMENTS 4,717,717 1/1988 Finkenaur ............................ 514/21

FOREIGN PATENT DOCUMENTS 267015    5/1988  European Pat. Off. .
281822    9/1988  European Pat. Off. .
308238A1  3/1989  European Pat. Off. .
0312208   4/1989  European Pat. Off. .

OTHER PUBLICATIONS

Journal of Cellular Physilosy, 128, 475 (1986).
Bioch. Biophys. Res. Commun. 151, 701 (1988).

*Primary Examiner*—Howard E. Schain
*Attorney, Agent, or Firm*—David G. Conlin; Gregory D. Williams

[57] ABSTRACT

Disclosed are (1) a stabilized FGF protein composition which comprises an FGF protein and water-insoluble hydroxypropyl cellulose; (2) a method for preparing a stabilized FGF protein composition, which comprises admixing an FGF protein with a water-insoluble hydroxypropyl cellulose; and (3) a method for stabilizing an FGF protein which comprises admixing an FGF protein with a water-insoluble hydroxypropyl cellulose, whereby the stabilized FGF protein can be provided. The composition is obtained in a solid state which has improved stability.

12 Claims, No Drawings

STABILIZED FGF COMPOSITION AND PRODUCTION THEREOF

BACKGROUND OF THE INVENTION

The present invention relates to a stabilized fibroblast growth factor (hereinafter briefly referred to as FGF) protein composition, a method for preparing a stabilized FGF protein composition, and a method for stabilizing an FGF protein.

FGF was first isolated as a factor exhibiting strong growth promoting action on fibroblasts such as BALB/c3T3 cells [D. Gospodarowicz, Nature 249, 123 (1974)]. It is now known that the FGF exhibits growth promoting action on almost all cells derived from mesoblast. FGF is classified into basic FGF (hereinafter briefly referred to as bFGF) and acidic FGF (hereinafter briefly referred to as aFGF), based on the isoelectric point thereof. bFGF and aFGF both have strong growth promoting action and plasminogen activator inducing action on vascular endothelial cells. Together, these actions suggest a potential for the application thereof as a drug for promoting angiogenesis, as a therapeutic drug for traumas, and as a preventive and therapeutic drug for thrombosis, arteriosclerosis, etc.

Previously, the FGFs were purified to homogeneity from organs derived from animals, such as bovine pituitary. However, supply of these FGFs was limited, and there was a fear of antigenicity due to their heterozoic origin. Recently, there has been developed a method for producing FGF in large quantities. The method involves using recombinant DNA techniques to express a cloned human FGF gene in microorganisms or in animal cells. [FEBS Letters 213, 189-194 (1987); European Patent Publication (hereinafter also referred to as EP Publication) No. 237,966)].

Another way of producing FGF in large quantity is stabilizing polypeptide producing factors using an aqueous medical composition comprising a water-soluble polysaccharides in amount sufficient for stabilizing a growth factor. This composition is disclosed as being effective against the declining of activities of mitogen of the polypeptide growing factor and the declining of bioactivities [Japanese Unexamined Patent Publication No. 63-152324/1988 corresponding to EP Publication No. 267,015].

Since most of the FGF proteins are very unstable, not only they are rapidly inactivated in aqueous solution, but also their bioactivity easily is decreased by lyophilization. Further, when the FGF proteins are administered for many hours as an intravenous drip, a reduction in titer during that time is unavoidable, which causes a major problem.

The above-described aqueous medical composition comprising water-soluble polysaccharides, especially in the case of cellulose derivatives of a degree of ether substitution of at least 0.35 ether groups per anhydroglucose unit in the cellolose chain, it is difficult to form a solid medical composition in powder when the base is an FGF protein. The titer of the composition is also lowered during mixing and drying process.

SUMMARY OF THE INVENTION

The present inventors have discovered that the stability of FGF proteins is surprisingly increased by admixing an FGF protein with a water-insoluble hydroxypropyl cellulose.

In particlular, the present inventors have succeeded in obtaining a solid composition having an improved stability of FGF protein as compared with that of the above-described aqueous medical composition comprising an FGF protein and water-soluble polysaccharides.

In accordance with the present invention, there is provided (1) a stabilized FGF protein composition which comprises an FGF protein and water-insoluble hydroxypropyl cellulose; (2) a method for preparing a stabilized FGF protein composition, which comprises admixing an FGF protein with a water-insoluble hydroxypropyl cellulose; and (3) a method for stabilizing an FGF protein, which comprises admixing an FGF protein with a water-insoluble hydroxypropyl cellulose.

DESCRIPTION OF THE PREFERRED EMBODIMENTS

The FGF proteins used in the present invention may include basic FGF and acidic FGF. The FGF protein used in the present invention include those derived from mammals. The mammals include human, monkey, pig, bovine, sheep and horse.

The FGF proteins include those extracted from various organs in which the presence of FGFs is already known, such as brain and pituitary.

Further, the FGF proteins include those obtained by the recombinant DNA technique [FEBS Letters 213, 189-194 (1987); EP Publication No. 237,966].

Hereinafter, the recombinant human basic FGF may be referred to as rhbFGF.

The FGF proteins used in the present invention include a FGF mutein.

Examples of the muteins of the FGFs used in the present invention include the muteins disclosed in Biochemical and Biophysical Research Communications 151, 701-708 (1988), EP No. 281,822 A2, and Japanese Patent Application No. 1-15662/1989 which corresponds to EP Publication No. 326,907 A1; and there may be included the muteins introduced by at least one glycosylation site diclosed in Japanese Patent Application No. 109014/1990 (filed on Apr. 25, 1990) which corresponds to European Patent Application No. 90107737.0 and U.S. patent application Ser. No. 511,469.

For example, the FGF muteins used in the present invention are obtained essentially by variations of the amino acid sequences of the original peptides or proteins. Such variations include addition of amino acid(s), deletion of constituent amino acid(s) and substitution of constituent amino acid(s) by different amino acid(s). Further, FGF muteins introduced by glycosylation site are included in such variations.

Such addition of amino acid(s) includes addition of at least one amino acid.

Such deletion of constituent amino acid(s) includes deletion of at least one FGF-constituent amino acid.

Such substitution of constituent amino acid(s) by different amino acid(s) includes substitution of at least one FGF-constituent amino acid by at least one different amino acid.

At least one amino acid in the mutein which has at least one amino acid added to the FGF excludes methionine derived from the initiation codon used for peptide expression and a signal peptide.

The number of the added amino acid(s) is at least one. However, it may be any number as long as FGF characteristics, such as one of the characteristics of angiogenesis, cell growth stimulating activity and cell differentiating activity, are not lost. More preferable amino acids include some or all of the amino acid sequences of proteins which have homology with the FGFs and which exhibit activities similar to those of the FGFs.

As for the number of the deleted FGF-constituent amino acid(s) in the mutein which lacks at least one FGF-constituent amino acid, it may be any number as long as FGF characteristics are not lost.

Examples of the deleted constituent amino acid include the 10 residues on the amino termial side of the human bFGF:

Met-Pro-Ala-Leu-Pro-Glu-Asp-Gly-Gly-Ser, the 14 residues on the amino terminal side of the human bFGF:

1
Met—Pro—Ala—Leu—Pro—Glu—Asp—Gly—Gly—Ser—Gly—Ala—

14
Phe—Pro, the 41 residues on the amino terminal side of the human bFGF:

1  2   3   4        41
Met—Pro—Ala—Leu— ... —Val, the 61 residues on the carboxyl terminal side of the human bFGF:

87   88         146  147
Lys—Cys—    —Val—Ser.

The muteins further include muteins lacking the 7 to 46 amino acid residues on the carboxyl side of the original peptide or protein of the bFGF.

Preferred examples of such deletion include deletion of the following amino acid sequences of the rhbFGF:

Amino acid sequence from amino acid No. 102 on
Amino acid sequence from amino acid No. 105 on
Amino acid sequence from amino acid No. 115 on
Amino acid sequence from amino acid No. 119 on
Amino acid sequence from amino acid No. 124 on
Amino acid sequence from amino acid No. 130 on
Amino acid sequence from amino acid No. 138 on As for the number of FGF-constituent amino acids prior to substitution in the mutein, which has at least one FGF-constituent amino acid substituted by at least one different amino acid, it may be any number as long as FGF characteristics are not lost.

Examples of the constituent amino acids prior to substitution include cysteine and cystine, but cysteine is preferable. The constituent amino acids other than cysteine prior to substitution include aspartic acid, arginine, glycine and valine.

When the constituent amino acid prior to substitution is cysteine, neutral amino acids are preferable as the substituted amino acids. The neutral amino acids include glycine, valine, alanine, leucine, isoleucine, tyrosine, phenylalanine, histidine, tryptophan, serine, threonine and methionine. Serine and threonine are particularly preferred.

When the constituent amino acid prior to substitution is any one other than cysteine, amino acids which are different, for example, in hydrophilicity, hydrophobicity or electric charge from the amino acid prior to substitution are selected as the substituting different amino acids. Specifically, when the amino acid prior to substitution is aspartic acid, the substituting amino acids include asparagine, threonine, valine, phenylalanine and arginine. In particular, asparagine and arginine are preferable.

When the amino acid prior to substitution is arginine, the substituting amino acids includes glutamine, threonine, leucine, phenylalanine and aspartic acid. Glutamine is especially preferable.

When the amino acid prior to substitution is glycine, the substituting amino acids include threonine, leucine, phenylalanine, serine, glutamic acid and arginine. Threonine is particularly preferred.

When the amino acid prior to substitution is serine, the substituting amino acids include methionine, alanine, leucine, cysteine, glutamine, arginine and aspartic acid. In particular, methionine is preferable.

When the amino acid prior to substitution is valine, the substituting amino acids include serine, leucine, proline, glycine, lysine and aspartic acid. Serine is especially preferred.

As the original constituent amino acids prior to substitution, aspartic acid, arginine, glycine, serine and valine are preferably selected.

As the substituting amino acids, asparagine, glutamine, arginine, threonine, methionine, serine and leucine are preferably selected.

The most preferred substituted muteins include a mutein in which cysteine, the constituent amino acid, is substituted by serine.

In the above substitution, the substitution of at least two constituent amino acids may be simultaneously carried out. In particular, it is preferable to substitute two or three constituent amino acids.

The muteins may be obtained by a combination of two or three of the above-mentioned addition, deletion and substitution.

A mutein is preferable in which at least one human bFGF-constituent amino acid is substituted by at least one different amino acid. In particular, rhbFGF mutein CS23 is preferable in which cysteine residues at the 70- and 88-positions of human bFGF are substituted by serine residues, respectively.

The FGF mutein has had introduced at least one glycosylation site. And the mutein may further have sugar chain(s).

The glycosylation sites include a site in which an amino acid sequence constituting the glycosylation site is represented by the following the formula:

Asn-X-Y (wherein X may be any amino acid residue, and Y is Thr, Ser or Cys).

X is preferably an amino acid other than Pro, and more preferably Gly, Tyr, Arg, Ser, Lys, Val or Ala and more preferably Gly, Lys, Val or Ala. Y is preferably Thr or Ser.

The sugar which is added to a FGF mutein may be any one found in known glycosylated proteins. Examples of such sugars include N-acetyl glycosamine, N- acetyl galactosamine, mannose, galactose, fucose and cyalic acid.

The number of sugars in a glycosyl chain is preferably at least one, and more preferably 10 to 20.

In order to produce the muteins, site-directed mutagenesis is employed. This technique is well-known and described in R. F. Lather and J. P. Lecoq, *Genetic Engineering*, pp. 31–50, Academic Press (1983). Mutagenesis directed to oligonucleotide is described in M. Smith and S. Gillam, *Genetic Engineering: Principles and Methods*, Vol. 3, pp. 1–32, Plenum Press (1981).

The production of a structural gene which encodes the mutein is carried out, for example, by the steps of:

(a) hybridizing a single-stranded DNA comprising a single strand of the structural gene of FGF with a mutagenic oligonucleotide primer(the above-mentioned primer is complementary to a region, including a codon for cysteine, to be replaced by this single strand, or including an anti-sense triplet which forms a pair with this codon in some cases, provided this does not apply to disparity with other codons for the amino acid than the above codon, or with the anti-sense triplet in some cases.), (b) elongating the primer using DNA polymerase to form a mutational heteroduplex, and (c) replicating this mutational heteroduplex.

Then, phage DNA for transferring the mutagenized gene is isolated and introduced into a plasmid.

A suitable host is transformed with the plasmid thus obtained, and the obtained transformant is cultivated in a medium, thereby being capable of producing the mutein.

Examples of the water-insoluble hydroxypropyl cellulose include low-substituted hydroxypropyl cellulose which is a low-substituted hydroxypropyl ether of cellulose.

The low-substituted hydroxypropyl cellulose contains not less than 5.0 percent and not more than 16.0 percent of hydroxypropoxyl group, when dried at 105° for 1 hour (Refer to the U.S. Pharmacopeia, the 21st revision, Supplement, pages 5180 to 5181; and the Japanese Pharmacopeia, the 11th revision, D-773 to D-780.).

Examples of low-substituted hydroxypropyl cellulose used in the present invention include low-substituted hydroxypropyl cellulose (LH-11, LH-20, LH-21, LH-22 and LH-31, Shin-Etsu Chemical, Japan)).

In the present invention, the weight ratio of the FGF protein to water-insoluble hydroxypropyl cellulose is preferably about 1:0.01 to 1,000,000, more preferably about 1:1 to 100,000, still more preferably about 1:500 to 20,000, and especially preferably about 1:500 to 10,000.

Further, the composition of the present invention may further contain one or more members selected from sugars, proteins, amino acids, sodium chloride and gum arabic.

The sugars include, for example, sucrose, trehalose, maltose, fructose, inositole and amylose. The proteins include, for example, casein, albumine, gelatin and egg white. The amino acids include, for example, cysteine, phenylalanine, leucine and glycine.

In the present invention, the weight ratio of FGF protein to sugars, proteins, amino acids, sodium chloride and/or gum arabic is preferably about 1:0.01 to 1,000,000, more preferably about 1:1 to 100,000, still more preferably about 1:500 to 20,000, and especially preferably about 1:500 to 10,000.

The compositions of the present invention are obtained by admixing the FGF protein with the water-insoluble hydroxypropyl cellulose, for example, by adding an aqueous solution of the FGF protein to water-insoluble hydroxypropyl cellulose in powder, followed by mixing. The pH of the aqueous solution of the FGF protein is preferably adjusted to about 3 to 10, more preferably to about 5 to 9.

The addition and the mixing are carried out, for example, at about 10° to 30° C., preferably at about 10° to 20° C.

The mixing is sufficiently performed by devices generally used for stirring and granulation [such as a mortar, a Pony mixer (Hosokawa Tekkosho, Japan), a Vertical granulator (Fuji Sangyo) and a Super mixer (Hosokawa Tekkosho)], by devices used for fluidized granulation [such as Glad (Okawara Seisakusho)] and by devices used for rolling granulation [such as CF (Freund)].

The compositions thus mixed are preferably dried or lyophilized at room temperature (about 10° to 30° C.) under reduced pressure (about 10 mmHg or less), whereby the solid compositions stabilized in bioactivity can be obtained.

Sugars, proteins, amino acids, sodium chloride and/or gum arabic may be simultaneously added when water-insoluble hydroxypropyl cellulose and FGF protein are mixed, or they may be mixed with water-insoluble hydroxypropyl cellulose, followed by adding FGF protein. The production method of the composition is carried out by similar method with that of the composition comprising water-insoluble hydroxypropyl cellulose and FGF protein.

In the above mixing, the aqueous solution of the FGF protein stabilized with glucan sulfate may be used.

Examples of the glucan sulfate include dextran sulfates, cyclodextrin sulfates and $\beta$-1,3-glucan sulfates. All of these are sulfuric ester derivative of polymer of D-glucose. The sulfur content in the glucan sulfate is preferably not less than about 3% by weight, more preferably about 12 to 20% by weight, most preferably about 16 to 20% by weight. In particular, dextran sulfate is preferable.

The dextran sulfates include a sulfate of dextran produced from sucrose by the action of a microorganism such as *Leuconostoc mesenteroides*. The dextran sulfate is a partial sulfates of dextran mainly containing $\alpha(1\rightarrow6)$ linkage, and the sulfur content therein is usually at least about 12% by weight, preferably about 16 to 20% by weight. The average molecular weight thereof is in the range of about 1,000 to 40,000,000, preferably in the range of 3,000 to 500,000. The dextran sulfate is very easily soluble in water, and is a compound already known in the art, which is manufactured by known methods per se.

Cyclodextrin in the cyclodextrin sulfate includes cyclodextrin produced from starch by the action of a microorganism such as *Bacillus macerans*. Cyclodextrin has a ring structure of D-glucose molecules linked by $\alpha(1\rightarrow4)$ linkage, and includes an $\alpha$-type (6 molecules), a $\beta$-type (7 molecules) and a $\gamma$-type (8 molecules). In this invention, any of these forms may be used.

Cyclodextrin sulfate is obtained by sulfation of cyclodextrin, and the sulfation is conducted according to methods already known in the art. The methods for sulfation include the methods described in U.S. Pat. No. 2,923,704 and Japanese Patent Unexamined Publication No. 50-36422/1975.

The sulfur content in the cyclodextrin sulfate is usually at least about 3% by weight, preferably about 12 to 24% by weight. The cyclodextrin sulfate has the property of being very soluble in water.

The degree of sulfation of the cyclodextrin sulfate may be any degree as long as the sulfur content is at least about 12% by weight. In particular, the cyclodextrin sulfate whose sulfur content is about 16 to 21% by weight are advantageously used. Mixtures of the sulfates different from one another in degree of sulfation may be used as such, or the purified sulfates having the single degree of sulfation may be used. The purification can be conducted, for example, by concentrating a reaction solution containing an alkali metal salt of β-cyclodextrin sulfate, evaporating it to dryness, dissolving the condensate in water, and mixing the resulting aqueous solution with a hydrophilic solvent to separate the desired product.

β-1,3-glucan in the β-1,3-glucan sulfate includes straight-chain β-1,3-glucans, which are produced by microorganisms belonging to Alcaligenes or Agrobacterium. These may be in the form of a low molecular weight polymer obtained by hydrolysis of the straight-chain β-1,3-glucans and similarly having a straight-chain β-1,3-glucan structure.

Curdlan (also known as a thermogelable polysaccharide PS and available from Wako Pure Chemical Industries Ltd. Japan) is known as a water-insoluble, thermogelable, unbranched glucan, and has straight-chain β-1,3-glucan linkage alone which is produced from a microbial strain belonging to Alcaligenes or Agrobacterium [Japanese Patent Publication Nos. 43- 7000/1968, 48-32673/1973 and 48-32674/1976].

The *Alcaligenes faecalis* var. Myxogenes NTK-u strain, the *Agrobacterium radiobacter* strain and the *Agrobacterium radiobacter* U-19 strain, which produce Curdlan, are cited in *American Type Culture Collection Catalogue of Strains*, the 15th edition (1982), as ATCC-21680, ATCC-6466 and ATCC-21679, respectively.

The properties of the partial hydrolyzate of Curdlan and the method for preparation thereof have already been described in detail in Japanese Patent Unexamined Publication No. 55- 83798/1980.

Thus, the straight-chain β-1,3-glucan is a compound represented by the following formula:

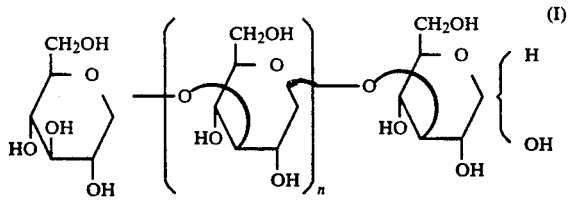

(I)

wherein n is an integer of 4 to about 1,000.

Any of the β-1,3-glucans described above may be used as long as the average degree of polymerization ($\overline{DP}$) thereof is not more than 1,000. In particular, there are advantageously used the partically hydrolyzed products thereof having an average degree of polymerization ($\overline{DP}$) of 6 to about 300, more preferably 15 to about 200.

n in the formula (I) has a relation to DP represented by the following equation:

$$\overline{DP} - 2 = n.$$

The sulfate of the straight-chain β-1,3-glucan is produced by sulfonation of the three hydroxyl groups of the intermediate monosaccharide unit of the β-1,3-glucan or its lower polymers and the hydroxyl groups of the monosaccharide units at both ends thereof. The sulfates having an average degree of substitution ($\overline{DS}$) of 0.5 to 3 per monosaccharide unit are usually used, and preferably ones having an average degree of substitution ($\overline{DS}$) of 1 to 2 are advantageously used.

Sulfation of straight-chain β-1,3-glucans or its low molecular weight polymer can be achieved by allowing a sulfating agent such as chlorosulfonic acid or sulfuric anhydride to act thereon, or by reacting a complex of sulfuric anhydride and an organic base such as pyridine, dimethylformamide, trimethylamine or dimethylaniline therewith [*J. Biol. Chem.* 239, 2986 (1964)].

The β-1,3-glucan sulfate is very soluble in water and low in toxicity. The sulfur content in β-1,3-glucan sulfates is usually at least about 5% by weight, preferably about 10 to 24% by weight.

Glucan sulfate is very low in toxicity to warm-blooded animals, and is therefore advantageous for parenteral or oral administration for the stabilized compositions comprising the FGF protein and the glucan sulfate.

Glucan sulfate may be used in the state of free or salt. Examples of such salts include sodium salts, potassium salts, ammonium salts and trimethylammonium salts.

When glucan sulfate is brought into contact with the FGF protein in aqueous media, the free glucan sulfate may be added thereto, followed by addition of a proper amount of an alkali or acid to give the desired pH. By the addition of alkali, the glucan sulfate may exist in the aqueous media in the form of either its salt or a mixture of the free dextran sulfate and its salt.

If the FGF protein is brought into contact with glucan sulfate in aqueous media in the presence of an additional dibasic or tribasic carboxylic acid, the FGF protein is advantageously more stabilized.

Examples of the dibasic carboxylic acids include tartaric acid, maleic acid, malic acid and fumaric acid.

The tribasic carboxylic acids include, for example, citric acid and isocitric acid.

The above carboxylic acids may be used in the form of either free compounds or their salts. Examples of such salts include sodium salts, potassium salts and ammonium salts.

Further, the free carboxylic acid may be added thereto, followed by addition of proper amounts of an alkali or acid to give the desired pH. By the addition of the alkali, the carboxylic acid may be exist in the aqueous media in the form of either its salt or a mixture of the free acid and its salt.

When the FGF protein is brought into contact with the glucan sulfate in aqueous media, it is preferred that the glucan sulfate is added in an amount of about 0.1 to 100 mol/mol, more preferably about 0.5 to 4 mol relative to 1 mol of FGF protein.

The concentration of the glucan sulfate in the aqueous media is preferably about 0.0005 to 5% by w/v, more preferably about 0.01 to 1% by w/v.

The concentration of the FGF protein in the aqueous media is preferably about 0.0005 to 5% by w/v, more preferably about 0.01 to 1% by w/v.

The concentration of the carboxylic acid in the aqueous media is preferably about 1 mM to 1M, more preferably about 10 mM to 500 mM.

Contact in the aqueous medium can be attained only by mixing the FGF protein, the glucan sulfate and the carboxylic acid as required with one another in the aqueous medium.

The aqueous media may be any media such as distilled water, physiological saline solution and glucose solution are preferably used. As the aqueous media, there can also be used buffers such as phosphate buffer and tris(hydroxymethyl)aminomethane-HCl buffer.

When the FGF protein, the glucan sulfate and the carboxylic acid as required are mixed with one another, they may be mixed as aqueous solutions, respectively, or may be mixed as solids, respectively, followed by dissolution in the aqueous medium. In mixing, the temperature is preferably about 0° to 40° C., and the pH is preferably in the range of about 3 to 10, more preferably in the range of about 5 to 9. The time taken to mix is usually about 1 to 30 minutes.

Thus, the aqueous solution of the FGF protein stabilized with glucan sulfate is obtained.

In the present invention, the above-described composition comprising FGF protein and water-insoluble hydroxypropyl cellulose may be further coated by an enteric polymer.

Examples of the enteric polymers used in the present invention include hydroxypropyl methyl cellulose phthalate, carboxymethyl ethyl cellulose, cellulose acetate phthalate, hydroxymethyl cellulose acetate succinate and acrylic polymers [such as methacrylic acid-ethyl acrylate copolymers (Eudragit L30D-55 and Eudragit L100-55), methacrylic acid-methyl acrylate copolymers (Eudragit L-100) and methacrylic acid-methyl methacrylate copolymers (Eudragit S100), Rohm, West Germany].

The coating is conducted by known methods. Namely, dispersions or solutions obtained by dispersing or dissolving the coating bases in water or organic solvents are sprayed on the tablets, the granules or the fine grains by pan coating methods, fluidized coating methods, the rolling coating methods or the like. When the compositions are coated with the coating agents, it is desirable that the temperature of the composition to be coated is about 25° to 70° C., preferably about 25° to 50° C. The coating amounts are about 20 to 300%, preferably 50 to 100% as the intestinally soluble polymers based on the compositions.

Further, the solid composition (powder) of the present invention and fatty acid ester of polyglycerol granules can also be heated and fluidized to obtain granules. According to the granules, the effective ingredient (FGF protein) of the solid composition of the present invention is stably eluted and released, and stabilized for a long time.

When the fatty acid ester of polyglycerol is a mixture, it does not show a clear melting point and is softened at a specific temperature in some cases. In this specification, the "melting point" includes a softening point which such a mixture shows.

The fatty acid ester of polyglycerol used above may be any of a monoester, a diester and a polyester as long as it is an ester formed by the combination of a polyglycerol with a fatty acid. The fatty acid ester of polyglycerol, unlike hardened oil and so on, has the characteristics of showing no crystal polymorphism and having little interaction with effective ingredients such as drugs.

The polyglycerin is "a polyhydric alcohol having n (in a cyclic polyglycerin) to n+2 (in a straight or branched polyglycerin) hydroxyl groups and n−1 (in a straight or branched polyglycerin) to n (in a cyclic polyglycerin) ether combinations in one molecule" [*Polyglycerin Ester*, p. 12, edited and published by Sakamoto Yakuhin Kogyo Co. Ltd., Japan (May 2, 1986)]. For example, compounds represented by the following formula can be used.

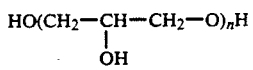

wherein n indicates a degree of polymerization and is an integer of 2 or more. n is normally 2 to 50, preferably 2 to 20, more preferably 2 to 10. The polyglycerol is straight or branched.

Specific examples of such polyglycerols include diglycerol, triglycerol, tetraglycerol, pentaglycerol, hexaglycerol, heptaglycerol, octaglycerol, nonaglycerol, decaglycerol, pentadecaglycerol, eicosaglycerol and triacontaglycerol. Of these polyglycerols, for example, tetraglycerol, hexaglycerol and decaglycerol are frequently used.

The fatty acids include, for example, saturated or unsaturated higher fatty acids having 8 to 40 carbon atoms, preferably 12 to 22 carbon atoms. Examples of such fatty acids include palmitic acid, stearic acid, oleic acid, linolic acid, linolenic acid, myristic acid, lauric acid, ricinolic acid, caprylic acid, capric acid and behenic acid. Of these fatty acids, stearic acid, oleic acid, lauric acid and ricinolic acid are preferred.

Specific examples of the fatty acid ester of polyglycerol include caprylyl mono(deca)glyceride, caprylyl di(tri)glyceride, lauryl mono(tetra)glyceride, lauryl mono(hexa)glyceride, lauryl mono(deca)glyceride, oleyl mono(tetra)glyceride, oleyl mono(hexa)-glyceride, oleyl mono(deca)glyceride, oleyl di(tri)glyceride, oleyl di(tetra)glyceride, oleyl sesqui(deca)glyceride, oleyl penta(tetra)glyceride, oleyl penta(hexa)glyceride, oleyl deca(deca)glyceride, linolyl mono(hepta)glyceride, linolyl di(tri)glyceride, linolyl di(tetra)glyceride, linolyl di(hexa)glyceride, stearyl mono(tetra)glyceride, stearyl mono(hexa)glyceride, stearyl mono(deca)glyceride, stearyl tri(tetra)glyceride, stearyl tri(hexa)glyceride, stearyl sesqui(hexa)glyceride, stearyl penta(tetra)glyceride, stearyl penta(hexa)glycedride, stearyl deca(deca)glyceride, palmityl mono(tetra)glyceride, palmityl mono(hexa)glyceride, palmityl mono(deca)glyceride, palmityl tri(tetra)glyceride, palmityl tri(hexa)glyceride, palmityl sesqui(hexa)glycoride, palmityl penta(tetra)glyccride, palmityl penta(hexa)glyceride and palmityl deca(deca)glyceride. Examples of the preferred fatty acid ester of polyglycerol include stearyl penta(tetra)glyceride (for example, PS-310, Sakamoto Yakuhin Co., Japan), stearyl mono(tetra)glyceride (for example, MS-310, Sakamoto Yakuhin Co.), stearyl penta(hexa)glyceride (for example, PS-500, Sakamoto Yakuhin Co.), stearyl acid sesqui(hexa)glyceride (for example, SS-500, Sakamoto Yakuhin Co.) and stearyl mono(deca)glyceride.

These fatty acid ester of polyglycerol may be used alone or as mixtures of two or more kinds.

The melting point of the fatty acid ester of polyglycerol is about 40° to 80° C., preferably about 40° to 60° C.

The molecular weight of the fatty acid ester of polyglycerol is usually 200 to 5,000, preferably 300 to 2,000. The hydrophile-lypophile balance (HLB) thereof is 1 to 22, preferably 1 to 15, and the elution rate of the effective ingredient of the powder can be controlled by adjusting the HLB. The HLB can also be adjusted by mixing two or more kinds of fatty acid ester of polyglycerol.

The fatty acid ester of polyglycerol can also be used together with lipids. Lipids useful in practicing the present invention may include water, insoluble materials, depending on the purpose of preparations and the like. The preferred softening point or melting point of the lipids is about 40° to 120° C., particularly about 40° to 90° C.

Specific examples of the lipids include the hardened products of fats and oils such as castor oil, cotton seed oil, soybean oil, rapeseed oil and beef tallow; waxes such as beeswax, carnauba wax, spermaceti, lecitin, paraffin and microcrystalline wax; fatty acids such as stearic acid and palmitic acid, or fatty acid salts such as sodium salts and potassium salts of fatty acids; fatty alcohols such as stearyl alcohol and cetyl alcohol; and glycerides. Of these lipids, there are preferable, for example, hardened cotton seed oil, hardened castor oil, hardened soybean oil, carnauba wax, microcrystalline wax, stearic acid and stearyl alcohol.

The ratio of the lipid to the fatty acid ester of polyglycerol is usually 100 parts by weight or less of lipid per 100 parts by weight of fatty acid ester of polyglycerol, and can be suitably selected within the above range.

In the preparation of the granulated compositions, spherical fatty acid ester of polyglycerol granules are preferably used to adhere the powders (the solid compositions of the present invention) in large amounts to the fatty acid ester of polyglycerol or to allow the esters to contain the powders in large amounts, and to obtain the granulated compositions corresponding to the shape and the size of the fatty acid ester of polyglycerol granules. When the spherical fatty acid ester of polyglycerol granules are used, large amounts of powders (the solid compositions of the present invention), for example, the powder constituting about 80% by weight of the whole granulated composition, can be incorporated therein. Moreover, the spherical granulated compositions relatively smooth in surface and narrow in size distribution can be obtained. In some cases, the powder can be incorporated therein so as to constitute more than 80% by weight, for example, about 85% by weight, of the whole granulated composition.

The spherical fatty acid ester of polyglycerol granules can be obtained, for example, by spray cooling, preferably spray chilling. The spray chilling can be carried out by rotating a disk such as an aluminum disk having a smooth surface and dripping the molten fatty acid ester of polyglycerol thereon. The rotary disk is not particularly limited in size, but is about 5 to 100 cm, preferably about 10 to 20 cm in diameter. The rotational speed of the rotary disk and the dripping rate of the molten fatty acid ester of polyglycerol can be determined depending on the desired size and the like of the granules. The rotational number of the rotary disk is usually about 10 to 6,000 rpm, preferably 900 to 6,000 rpm, more preferably 1,000 to 3,000 rpm. The molten fatty acid ester of polyglycerol can be dripped at a constant rate, for example, of about 2 to 200 g/min, preferably about 5 to 100 g/min.

The size of the fatty acid ester of polyglycerol granules can be selected according to the desired size of the granulated composition and is not particularly limited, but is usually about 10 to 150 meshes, preferably about 25 to 100 meshes.

The solid compositions (powders) of the present invention can be used together with powdery diluents. Examples of such diluents include excipients such as lactose, cornstarch, Avicel (microcrystalline cellulose: Asahi Chemical Industry, Japan), powder sugar and magnesium stearate; binders such as starch, gelatin, gum arabic powder, methyl cellulose, carboxymethyl cellulose sodium, hydroxypropyl methyl cellulose and polyvinyl pyrrolidon; disintegrators such as carboxymethyl cellulose calcium and low substituted-hydroxypropyl cellulose; coloring agents; flavoring agents; absorbents; preservatives; wetting agents; antistatic agents; and disintegration delaying agents.

The ratio of the powder (the solid composition of the present invention) to the above fatty acid ester of polyglycerol can be established depending on the desired size of the granulated composition, the content of the drug active ingredient and the like, but is usually 10 to 1,000 parts by weight, preferably 50 to 500 parts by weight of the powder per 100 parts by weight of the fatty acid ester of polyglycerol.

The granulation by heating and fluidizing can be conducted according to conventional fluidized-bed granulating methods. The heating temperature in the granulating methods is near the melting point of the above fatty acid ester of polyglycerol ester, preferably within the range from the melting point of the fatty acid ester of polyglycerol to the temperature 5° C. lower than the melting point. If the heating temperature is too high, the fatty acid ester of polyglycerol granules tend to coalesce by fusion to form a granulated composition wide in size distribution. On the other hand, if the heating temperature is too low, it is difficult to granulate the powder (the solid composition of the present invention) with the fatty acid ester of polyglycerol granules.

The granulation can be performed by floating the fatty acid ester of polyglycerol granules and the powder (the solid composition of the present invention) to form a fluidized bed, and by heating and fluidizing them at a required temperature. It can be confirmed by the presence or absence of the powder particles whether or not the granulation is completed.

The granulated compositions thus obtained are usually fine-grained or granular.

When the granulated composition is observed under a microscope, it usually has a shape corresponding to the shape of the fatty acid ester of polyglycerol granule, and it seems that the powder (solid composition of the present invention) is at least partially embedded in the fatty acid ester of polyglycerol granule, preferably involved therein to coaleace.

The compositions of the present invention thus obtained are solid.

The compositions of the present invention include pharmaceutical compositions containing the above solid compositions (for example, ointments and suppositories). Namely, in the case of the ointments, the solid compositions of the present invention are dispersed in bases for the ointments. In the case of the suppositories, the solid compositions of the present invention are dispersed in bases for the suppositories.

As the present FGF composition is stabilized, it can be advantageously used as a medicament.

The stabilized FGF protein compositions of the present invention can be safely administered parenterally or orally to warm-blooded animals (such as human, mouse, rat, hamster, rabbit, dog and cat) as such or with pharmacologically permissible additives (such as carriers, excipients and diluents), as pharmaceutical compositions (such as tablets, capsules, granules, fine grains, powders, ointments and suppositories).

Such preparations can be formulated into the forms suitable for oral administration such as tablets, capsules, powders, granules and fine grains in accordance with known methods. In these cases, as additives are used excipients (such as lactose, cornstarch, light silica and fine crystalline cellulose), binders (such as alpha starch, methyl cellulose, carboxymethyl cellulose, hydroxypropyl cellulose, hydroxypropyl methyl celulose and polyvinyl pyrrolidone), disintegrators (such as carboxymethyl cellulose calcium, starch and low-substituted hydroxypropyl cellulose), surface active agents [such as Tween 80 (Kao Atlas, Japan), Pluronic F68 (Asahi Denka Kogyo, Japan) and polyoxyethylene-polyoxypropylene copolymer], antioxidants (such as L-cysteine, sodium sulfite and sodium ascorbate) and lubricants (such as magnesium stearate and talc).

As to the tablets, the granules and the fine grains, coating may be carried out in accordance with known methods for the purpose of masking tastes or giving intragastric solubility, intestinal solubility or increasing sustained release. As the coating agents are used, for example, hydroxypropyl methyl cellulose, ethyl cellulose, hydroxymethyl cellulose, hydroxypropyl cellulose, polyoxyethylene glycol, Tween 80, Pluronic F68, castor oil, cellulose acetate phthalate, hydroxypropyl methyl cellulose phthalate, hydroxypropyl methyl cellulose acetate succinate, acrylic polymers (Eudragit L100-SS and L-100, Rohm, West Germany), carboxymethyl ethyl cellulose, polyvinyl acetal diethylamino acetate, waxes and pigments such as talc, titanium oxide and iron oxide red. These coating agents may be applied in one or more layers, alone or in combination of two or more agents.

The coating is conducted by known methods. Namely, dispersions or solutions obtained by dispersing or dissolving the coating bases in water or organic solvents are sprayed on the tablets, the granules or the fine grains by pan coating methods, fluidized coating methods or rolling coating methods. The tablets, the granules and the fine grains are preferably coated at about 25° to 70° C., more preferably at about 25° to 50° C.

Further, ointments and suppositories can be prepared according to known methods using the following additives.

Examples of the additives used when the ointments are prepared include vaseline, beweswax, paraffin, liquid paraffin, cholesterol, stearyl alcohol, lanolin, cetyl alcohol and polyethylene glycol.

Examples of the additives used when the suppositories are prepared include cacao butter, hydrogenated vegetable oils, monoglycerides, triglycerides, glycerogelatin and polyethylene glycol.

The FGF protein compositions of the present invention have growth promoting action on fibroblasts, high stability and low toxicity. Therefore, the FGF protein compositions can be used as therapeutic promoting drugs for burns, traumas, postoperative tissues and the like, or therapeutic drugs for thrombosis, arteriosclerosis and the like by arterializing action. Also, they can be used as reagents for promoting cell cultivation.

When the FGF protein compositions of the present invention are used as the above-mentioned drugs, they are administered, for example, to the above-mentioned warm-blooded animals in an appropriate amount ranging from about 1 ng/kg to 100 μg/kg daily as the FGF protein, taking into account the route of administration, symptoms, etc.

Recombinant human bFGF mutein CS23 (hereinafter also referred to as rhbFGF mutein CS23) used in the Examples hereinafter described is prepared by the method described in *Biochemical and Biophysical Research Communications* 151, 701-708 (1988) or the method described in European Patent Publication No. 281,822 A2. The rhbFGF mutein CS23 used in the Examples hereinafter described was prepared and purified by the methods described in European Patent Publication No. 281,822 A2, Examples 1, 2, 7 and 24, using transformant *Escherichia coli* MM294/pTB762 (IFO 14613, FERM BP-1645).

The transformant *Escherichia coli* MM294/pTB762 described above was deposited with the Institute for Fermentation, Osaka (IFO), Japan and with the Fermentation Research Institute, Agency of Industrial Science and Technology, Ministry of International Trade and Industry (FRI), Japan. The accession number and the deposit date are shown in Table 1. As to the deposit in FRI, the deposit was initially made under accession number denoted by FERM P number. Said deposit was converted to the deposit under Budapest Treaty and the transformant has been stored at FRI under accession number denoted by FERM BP.

TABLE 1

| Transformant | IFO | FRI | |
|---|---|---|---|
| E. coli MM294/ pTB762 | IFO 14613 (May 27, 1987) | FERM P-9409 (June 11, 1987) | FERM BP-1645 |

REFERENCE EXAMPLE 1

The FGF activity in Examples described below was measured by the following method.

Samples diluted in 2-fold step with DMEM medium containing 10% calf serum were added to a Nunc 96-well microtiter plate (flat base) in an amount of 50 μl per well, and then each well was seeded with 50 μl ($2 \times 10^3$ cells) of fetal bovine cardiac endotherial cells (CRL1395) purchased from American Type Culture Clollection, followed by cultivation for 3 days. Then, to each well was added 20 μl of MTT [3-(4,5-dimethyazolyl-2-yl)-2,5-diphenyltetrazolium bromide] [*Journal of Immunological Method* 93, 157 (1986)] solution (5 mg/ml PBS, Sigma). After 4.5 hours, 100 μl of 10% SDS-0.01 N HCl was added thereto, and then the microtiter plate was allowed to stand overnight. Thereafter, the absorbance at 590 nm was measured by using Titertek Multiscan [Tada et al., *Journal of Immunological Method* 93, 157 (1986)].

EXAMPLE 1

Sodium dextran sulfate having a mean molecular weight of 7,500 (Seikagaku Kogyo, Japan) was added to a 50 mM sodium citrate solution (pH 8.0) containing rhbFGF mutein CS23 in a concentration of 450 μg/ml so as to give a concentration of 210 μg/ml. Then, 1 ml of the resulting solution was added to 5 g of low-substituted hydroxypropyl cellulose (hereinafter referred to as L-HPC) (LH-20, hydroxypropoxyl group:13.0 to 16.0%, Shin-Etsu Chemical), followed by sufficient stirring. The mixture thus obtained was dried at room temperature (about 20° C.) under reduced pressure (about 5 mm Hg) for 20 hours to obtain a crude powder composition containing rhbFGF mutein CS23 and L-HPC.

As a control, a powder composition containing rhbFGF mutein CS23 and lactose was prepared in the same manner as the above method except that 5 g of lactose was used in place of L-HPC.

The remaining activity of these compositions was measured by the method described in Reference Example 1. The results are shown in Table 2.

TABLE 2

| Additive | Remaining FGF Activity (%) |
|---|---|
| L-HPC | 127 |
| Lactose | 8 |

EXAMPLE 2

Sodium dextran sulfate having a mean molecular weight of 7,500 was added to a 50 mM sodium citrate solution (pH 8.0) containing rhbFGF mutein CS23 in a concentration of 500 μg/ml so as to give a concentration of 233 μg/ml. Then, 1 ml portions of the resulting solution were added to 5 g of L-HPC (LH-11, hydroxypropoxyl group: 10.0 to 13.0%, Shin-Etsu Chemical) and to 5 g of lactose, respectively, followed by sufficient stirring. The mixtures thus obtained were lyophilized to obtain powder compositions containing rhbFGF mutein CS23 and L-HPC, and rhbFGF mutein CS23 and lactose, respectively.

The remaining activity of these compositions is shown in Table 3.

TABLE 3

| Additive | Remaining FGF Activity (%) |
|---|---|
| L-HPC | 85 |
| Lactose | 11 |

EXAMPLE 3

Using the powder composition containing rhbFGF mutein CS23 and L-HPC obtained in Example 1, granules were prepared by the following method.

Namely, 85 g of nonpareils (20 to 28 meshes) was placed in a mini CF device (Freund), and coated with the powder having the following composition by sprinkling at a rate of 5 g/min at a rotational speed of a rotor of 400 rpm while spraying 50 ml of a 1% (w/v) hydroxypropyl cellulose (hydroxypropoxyl group:53.4 to 77.5%) solution at a rate of 2.5 ml/min. The resulting product was dried under vacuum at 40° C. for 16 hours, followed by sieving through a round sieve to obtain spherical granules having a particle size of 12 to 32 meshes.

| [Powder] | |
|---|---|
| Powder composition containing the rhbFGF mutein CS23 obtained in Example 1 | 20 g |
| Fine granulated sugar | 20 g |
| Corn Starch | 20 g |

Then, 60 g of the granules thus obtained was placed in a mini CF device (Freund), and provided with an intestinally soluble coating by spraying the intestinally soluble film solution having the following composition at a rate of 5 ml/min at a rotational speed of a rotor of 400 rpm, adjusting the air temperature to 40° C. and the granule temperature to 35° C., to obtain intestinally soluble granules.

| [Intestinally Soluble Film Solution] | |
|---|---|
| Hydroxypropyl methyl cellulose phthalate | 20 g |
| Castor oil | 2 g |
| Talc | 0.4 g |
| Acetone | 200 ml |

EXAMPLE 4

2 ml of 50 mM sodium citrate solution (pH 7.0) containing rhbFGF mutein CS23 at a concentration of 1 mg/ml was added to 2 g of L-HPC (LH-20, Shin-Etsu Chemical), and the mixture was sufficiently stirred, followed by drying at room temperature (about 20° C.) under reduced pressure (about 5 mm Hg) for 20 hours to obtain a powder composition. The remaining activity of the resulting composition was 100%.

EXAMPLE 5

2 ml of 50 mM sodium citrate solution (pH 7.0) containing rhbFGF mutein CS23 at a concentration of 1 mg/ml was added to a mixture of 1.6 g of L-HPC (LH-20, Shin-Etsu Chemical) and 0.4 g of powder sugar (pulverized sucrose) as a saccharide, and the resulting mixture was sufficiently stirred, followed by drying at room temperature (about 20° C.) under reduced pressure (about 5 mm Hg) for 20 hours to obtain a powder composition. The composition thus obtained showed the following remaining activity immediately after preparation, after 2 months at 40° C. and after 6 months at 40° C.

| | L-HPC + Sugar Powder |
|---|---|
| Immediately after preparation | 95% |
| After 2 months at 40° C. | 81% |
| After 6 months at 40° C. | 81% |

EXAMPLE 6

(1) 500 g of stearyl mono(tetra)glyceride (MS-310, Sakamoto Yakuhin Co.) was added to 500 g of stearyl penta(tetra)glyceride (PS-310, Sakamoto Yakuhin Co.), and the mixture was heated at 90° C. to melt it. The resulting melt was dripped at a rate of 20 g/minute on an aluminum disk 15 cm in diameter rotating at 1,000 rpm to prepare spherical fatty acid ester of polyglycerol granules which pass through a 32-mesh sieve, but does not pass through a 42-mesh sieve.

100 g of the spherical fatty acid ester of polyglycerol granules obtained above, 5 g of the powder composition obtained in Example 4 and 95 g of L-HPC (LH-20, Shin-Etsu Chemical) were placed in a fluidized granulator (type FD-3S, Fuji Sangyo). Setting the supply air temperature to 54° C., the mixture was heated and fluidized. After it was confirmed that L-HPC particles floating in a fluidized bed had disappeared, the supply of heat was stopped and the cooling was carried out, thereby obtaining granules.

(2) 100 g of the granules of rhbFGF mutein CS23 obtained in the above item (1) was placed in the fluidized granulator (type FD-3S, Fuji Sangyo), and coated with a coating solution [a solution of 100 g of hydroxypropyl methyl cellulose phthalate HP-55S (Shin-Etsu Chemical) in 1 liter of a 1:1 mixture of acetone and ethanol) at a solution supply rate of 2 g/minute at a supply air temperature of 48° C. to obtain a coated granule composition containing rhbFGF mutein CS23.

EXAMPLE 7

2 ml of 50 mM sodium citrate solution (pH 7.0) containing rhbFGF mutein CS23 at a concentration of 1 mg/ml was added to a mixture of 1.6 g of L-HPC (LH-20, Shin-Etsu Chemical) and 0.4 g of human serum albumin (HSA), casein or purified gelatin as a protein, and the resulting mixture was sufficiently stirred, followed by drying at room temperature (about 20° C.) under reduced pressure (about 5 mm Hg) for 20 hours to obtain a respective powder compositions.

EXAMPLE 8

2 ml of 50 mM sodium citrate solution (pH 7.0) containing rhbFGF mutein CS23 at a concentration of 1 mg/ml was added to a mixture of 1.6 g of L-HPC (LH-20, Shin-Etsu Chemical) and 0.4 g of sodium chloride, and the resulting mixture was sufficiently stirred, followed by drying at room temperature (about 20° C.) under reduced pressure (about 5 mm Hg) for 20 hours to obtain a powder composition.

EXAMPLE 9

2 ml of 50 mM sodium citrate solution (pH 7.0) containing rhbFGF mutein CS23 at a concentration of 1 mg/ml was added to a mixture of 1.6 g of L-HPC (LH-20, Shin-Etsu Chemical) and 0.4 g of L-cysteine as an amino acid, and the resulting mixture was sufficiently stirred, followed by drying at room temperature (about 20° C.) under reduced pressure (about 5 mm Hg) for 20 hours to obtain a powder composition.

EXAMPLE 10

2 ml of 50 mM sodium citrate solution (pH 7.0) containing rhbFGF mutein CS23 at a concentration of 1 mg/ml was added to a mixture of 1.2 g of L-HPC (LH-20, Shin-Etsu Chemical), 0.4 g of L-cysteine and 0.4 g of sodium chloride, and the resulting mixture was sufficiently stirred, followed by drying at room temperature (about 20° C.) under reduced pressure (about 5 mm Hg) for 20 hours to obtain a powder composition.

EXAMPLE 11

2 ml of 50 mM sodium citrate solution (pH 7.0) containing rhbFGF mutein CS23 at a concentration of 1 m9/ml was added to a mixture of 1.2 g of L-HPC (LH-20, Shin-Etsu Chemical), 0.4 g of L-cysteine and 0.4 g of powder sugar, and the resulting mixture was sufficiently stirred, followed by drying at room temperature (about 20° C.) under reduced pressure (about 5 mm Hg) for 20 hours to obtain a powder composition.

EXAMPLE 12

2 ml of 50 mM sodium citrate solution (pH 7.0) containing rhbFGF mutein CS23 at a concentration of 1 mg/ml was added to a mixture of 1.6 g of L-HPC (LH-20, Shin-Etsu Chemical) and 0.4 g of gum arabic, and the resulting mixture was sufficiently stirred, followed by drying at room temperature (about 20° C.) under reduced pressure (about 5 mm Hg) for 20 hours to obtain a powder composition.

EXPERIMENTAL EXAMPLE 1

Sodium dextran sulfate having an average molecular weight of 7,500 was added to a 50 mM sodium citrate solution (pH 8.0) containing rhbFGF mutein CS23 in a concentration of 200 μg/ml so as to give a concentration of 93.2 μg/ml. Then, 1 ml portions of the resulting solution were added to 1 g of L-HPC (LH-20) and to 1 g of hydroxypropyl cellulose (hydroxypropoxyl group:61 %), respectively. The resulting solution was stirred sufficiently. The mixtures thus obtained were dried at room temperature for 20 hours under reduced pressure (about 20° C., about 5 mmHg) to give powder compositions containing rhbFGF mutein CS23 and L-HPC, and rhbFGF mutein CS23 and hydroxypropyl cellulose, respectively. The remaining activity of these compositions is shown in Table 4.

TABLE 4

| Additive | Remaining FGF Activity (%) |
|---|---|
| L-HPC | 100 |
| Hydroxypropyl cellulose | 44 |

The following references, which are referred to for their disclosures at various points in this application, are incorporated herein by reference.

Nature 249, 123 (1974)
FEBS Letters 213, 189–194 (1987)
EP-237,966
Japanese Unexamined Patent Publication No. 63-152324/1988 corresponding to EP Publication No. 267,015
Biochemical and Biophysical Research Communications 151, 701–708 (1988)
EP No. 281,822 A2
Japanese Patent Application No. 1-15662/1989 corresponding to EP Publication No. 326,907 A1
Japanese Patent Application No. 109014/1990 (filed on Apr. 25, 1990 corresponding to European Patent Application No. 90107737.0 and U.S. patent application Ser. No. 511,469
Genetic Engineering, pp. 31–50, Academic Press (1983)
Genetic Engineering: Principles and Methods, Vol. 3, pp. 1–32, Plenum Press (1981)
Japanese Pharmacopeia, the 11th revision, D-773 to D-780
The U.S. Pharmacopeia, the 21st revision, Supplement, pages 5180 to 5181
U.S. Pat. No. 2,923,704
Japanese Unexamined Publication No. 50-36422/1975
Japanese Patent Publication Nos. 43-7000/1968, 48-32673/1973 and 48-32674/1976
J. Biol. Chem. 239, 2986 (1964)
Japanese Patent Unexamined Publication No. 55-83798/1980
Polyglycerin Ester, p. 12, edited and published by Sakamoto Yakuhin Kogyo Co. Ltd., Japan (May 2, 1986)
Journal of Immunological Method 93, 157 (1986)

What is claimed is:

1. A stabilized FGF protein composition which comprises an FGF protein and low-substituted hydroxypropyl cellulose which contains not less than 5.0 percent and not more than 16.0 percent of hydroxypropyl group.
2. A composition in accordance with claim 1, wherein the FGF protein is an FGF mutein.
3. A composition in accordance with claim 2, wherein the FGF protein is a mutein at least one human basic FGF-constituent amino acid of which is substituted by at least one different amino acid.

4. A composition in accordance with claim 1, which is further coated by an enteric polymer.

5. A method for preparing a stabilized FGF protein composition, which comprises admixing an FGF protein protein and low substituted hydroxypropyl cellulose which contains not less than 5.0 percent and mot more than 16.0 percent of hydroxypropyl group.

6. A method in accordance with claim 5, wherein the FGF protein is an FGF mutein.

7. A method in accordance with claim 6, wherein the FGF protein is a mutein at least one human basic FGF-constituent amino acid of which is substituted by at least one different amino acid.

8. A method in accordance with claim 5, which comprises further coating the composition by an enteric polymer.

9. A method for stabilizing an FGF protein, which comprises admixing an FGF protein and hydroxypropyl cellulose which contains not less than 5.0 percent and not more than 16.0 percent of hydroxypropyl group.

10. A method in accordance with claim 9, wherein the FGF protein is an FGF mutein.

11. A method in accordance with claim 10, wherein the FGF protein is a mutein at least one human basic FGF-constituent amino acid of which is substituted by at least one different amino acid.

12. A method in accordance with claim 9, which comprises further coating the composition by an enteric polymer.

* * * * *